US00PP11957P2

(12) United States Plant Patent
Burke

(10) Patent No.: US PP11,957 P2
(45) Date of Patent: Jun. 26, 2001

(54) LYCIANTHES PLANT NAMED 'VARIEGATED SPLASH'

(75) Inventor: John Burke, Riverside, CA (US)

(73) Assignee: Hines Nurseries, Inc., Irvine, CA (US)

( * ) Notice: Subject to any disclaimer, the term of this patent is extended or adjusted under 35 U.S.C. 154(b) by 0 days.

(21) Appl. No.: 09/460,004

(22) Filed: Dec. 13, 1999

(51) Int. Cl.[7] ..... A01H 5/00

(52) U.S. Cl. ..... Plt./226

(58) Field of Search ..... Plt./226, 263

*Primary Examiner*—Bruce R. Campell
*Assistant Examiner*—Kent L. Bell
(74) *Attorney, Agent, or Firm*—C. A. Whealy

(57) ABSTRACT

A distinct cultivar of Lycianthes plant named 'Variegated Splash', characterized by its upright and spreading plant habit; unique green, pale yellow and ivory variegated foliage; attractive dark purple flowers; and good garden performance.

1 Drawing Sheet

BACKGROUND OF THE INVENTION

The present invention relates to a new and distinct cultivar of Lycianthes plant, botanically known as *Solanum rantonnetii,* and hereinafter referred to by the cultivar name 'Variegated Splash'.

The new Lycianthes is a naturally-occurring whole plant mutation of an unidentified selection of *Solanum rantonnetii* (not patented) with solid green leaves. The new Lycianthes was discovered and selected by the Inventor in 1998, within a population of plants of the unidentified *Solanum rantonnetii* selection grown in a cultivated area in Irvine, Calif. The new Lycianthes was selected on the basis of its unique variegated foliage.

Asexual reproduction of the new cultivar by terminal cuttings taken at Irvine, Calif., has shown that the unique features of this new Lycianthes are stable and reproduced true to type in successive generations.

SUMMARY OF THE INVENTION

Plants of the cultivar 'Variegated Splash' have not been observed under all possible environmental conditions. The phenotype may vary somewhat with variations in environment such as temperature, light intensity, daylength, and fertility level without, however, any variance in genotype.

The following traits have been repeatedly observed and are determined to be the unique characteristics of 'Variegated Splash'. These characteristics in combination distinguish 'Variegated Splash' as a new and distinct cultivar:

1. Upright and spreading plant habit.
2. Unique green, pale yellow and ivory variegated foliage.
3. Attractive dark purple flowers.
4. Good garden performance.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description which accurately describe the actual colors.

The photograph at the top of the sheet comprises a side perspective view of a typical plant of the new Lycianthes.

The photograph at the bottom of the sheet comprises a close-up view of typical flowers and leaves of the new Lycianthes.

DETAILED BOTANICAL DESCRIPTION

In the following description, color references are made to The Royal Horticultural Society Colour Chart except where general terms of ordinary dictionary significance are used.

Plants used for the description were one-year old and were grown under outdoor production conditions during the spring and early summer in Irvine, Calif.

Botanical classification: *Solanum rantonnetii* cultivar 'Variegated Splash'.

Parentage: Naturally-occurring whole plant mutation of an unidentified selection of *Solanum rantonnetii* (not patented).

Propagation:

*Type.*—By stem cuttings.

*Time to initiate roots.*—About 10 days at temperatures about 22° C.

*Time to develop roots* (*time to produce a rooted liner*).—About 25 days at temperatures about 22° C.

*Root description.*—Fine, freely branching.

Plant description:

*Crop time.*—From cuttings, about 26 weeks are required to produce a flowering plant in a one-gallon container.

*Form.*—Upright and outwardly spreading subshrub.

*Plant height.*—About 27.5 cm.

*Plant width.*—About 48 cm.

*Growth rate.*—Slow.

*Lateral branches.*—Quantity: Very freely branching; pinching enhances lateral branch development; laterals may form at every node. Length, pinched shoots: About 50 cm. Diameter, primary stem: About 8 mm. Internode length: About 1.1 cm. Texture: Glabrous; narrow longitudinal ridges on young stems. Color: 195A.

*Foliage description.*—Leaves simple, generally symmetrical, alternate and long persisting. Moderately tolerant to stresses. Length: About 3 cm. Width:

About 2 cm. Shape: Mostly elliptic to ovate. Apex: Rounded acute. Base: Attenuate. Margin: Entire; somewhat sinuate. Texture: Smooth, matte; very scarce pubescence mostly on lower surface. Color: Actual variegation patterns vary. Young foliage, upper surface: Margin, 9C; center, random areas of 139C and 145A. Young foliage, lower surface: Margin, 9D; center, random areas of 138B and 145C. Mature foliage, upper surface: Margin, 4D; center, random areas of 147C and 147B. Mature foliage, lower surface: Margin, 4D; center, random areas of 147D and 147C. Venation, both surfaces: 147D. Petiole: Length: About 6.5 mm. Diameter: About 1.5 mm. Color: 189A.

Flower description:

*Flower type and habit.*—Rounded dark purple flowers arranged in axillary cymes; flowers face outward or upright. Corolla, flattened trumpet, 5-lobed; calyx five-cleft. Individual flowers last about one or two days on the plant. Not persistent.

*Natural flowering season.*—In warmer climates (zone 10) and in greenhouses, flowering year-round. In cooler climates, flowering occurs from spring to fall.

*Quantity.*—About two or three flowers per axillary cyme.

*Fragrance.*—None detected.

*Flower buds.*—Length (showing color): About 7 mm. Diameter (showing color): About 4 mm. Shape: Ovoid. Color: 92B.

*Flowers size.*—Diameter: About 2.4 cm. Depth: About 1.8 cm.

*Petals.*—Quantity: Five, fused. Length (beyond throat): About 1.4 cm. Width: At apex, about 1.8 cm; at base, about 2 mm. Shape: Deltoid. Apex: Rounded. Margin: Entire; sinuate. Texture: Smooth, velvety. Color: When opening, upper surface: 86A to 86B. When opening, lower surface: 86A. Fully opened, upper surface: 86A with small yellow, 10A, base. Fully opened, lower surface: 86B; central stripe, 86A.

*Calyx.*—Calyx length: About 4 mm. Calyx diameter: About 5 mm. Shape: Campanulate; sepals, narrow and fused at base. Sepal quantity: Five. Sepal apex: Acuminate. Sepal margin: Entire. Sepal texture: Smooth. Sepal color, upper and lower surfaces: 145C.

*Peduncle.*—Strength: Slender and flexible, but strong. Length: About 1.8 cm. Angle: Upright. Color: 138C.

*Reproductive organs.*—Androecium: Stamen number: Five. Anther shape: Elongated ovate. Anther size: About 2 by 3 mm. Anther color: 14A. Pollen: Moderate. Pollen color: 8A. Gynoecium: Pistil number: One. Pistil length: About 1.1 cm. Stigma color: 91C. Style length: About 5 mm. Style color: 145C. Ovary color: 145D.

*Seed/fruit development.*—Seed/fruit development has not been observed.

Disease resistance: Under commercial conditions, resistance to pathogens common to *Solanum rantonnetii* has been observed.

Winter hardiness: Hardy to U.S.D.A. Hardiness Zone 9.

It is claimed:

1. A new and distinct cultivar of Lycianthes plant named 'Variegated Splash', as illustrated and described.

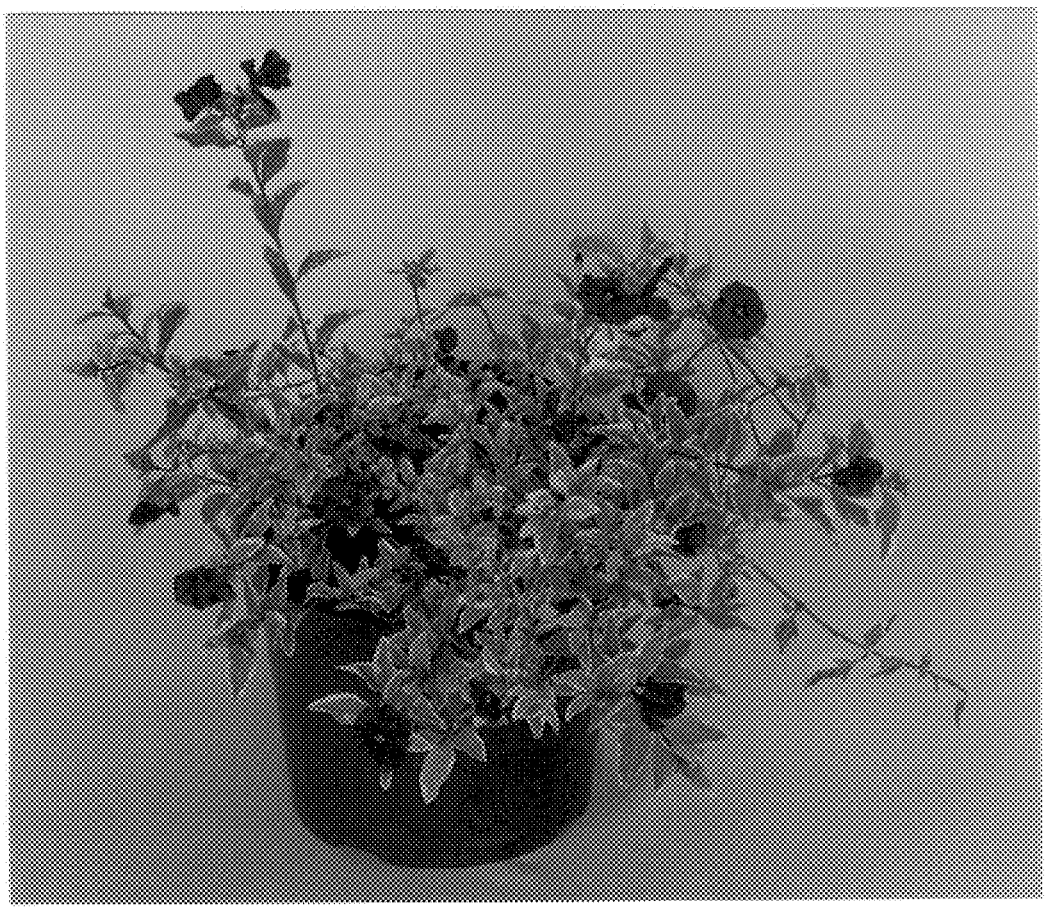
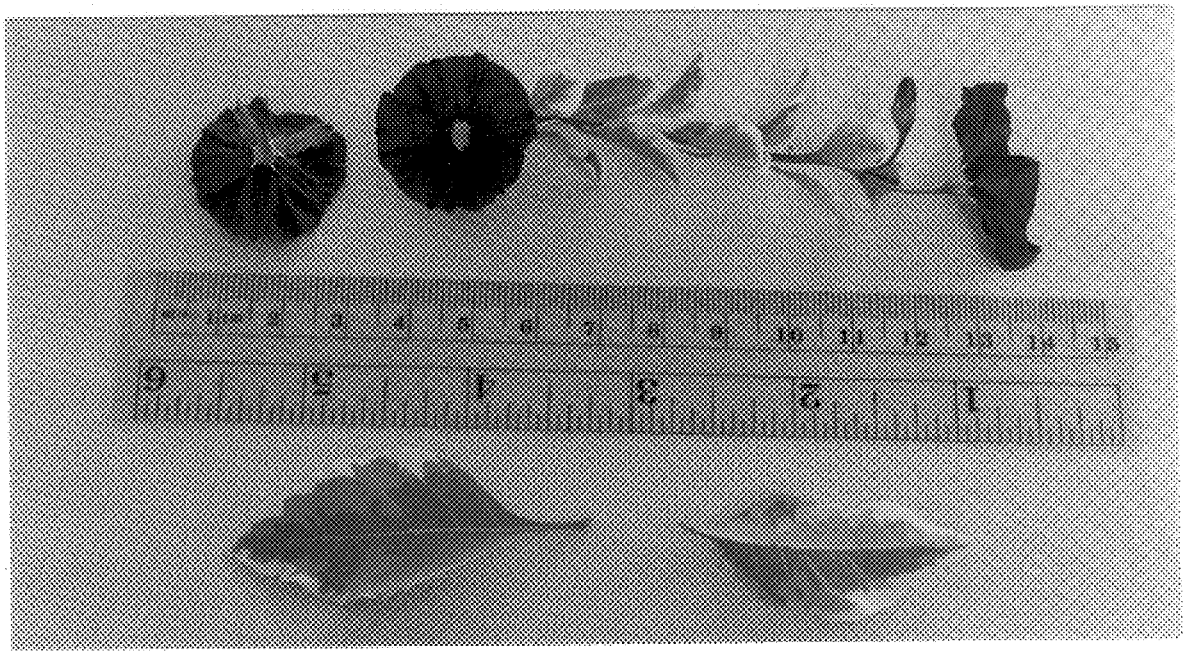

* * * * *